United States Patent [19]

Laurent

[11] Patent Number: 5,439,920
[45] Date of Patent: Aug. 8, 1995

[54] 1,2,5,6-TETRAHYDROPYRIDINE DERIVATIVE, PROCESS FOR PREPARING IT AND ITS APPLICATIONS IN THERAPY

[75] Inventor: Philippe Laurent, Oullins, France

[73] Assignee: Laboratoire L. Lafon, Maisons Alfort, France

[21] Appl. No.: 215,782

[22] Filed: Mar. 22, 1994

[30] Foreign Application Priority Data

Mar. 31, 1993 [FR] France ............... 93 03783

[51] Int. Cl.$^6$ .................. C07D 211/70; A61K 31/44
[52] U.S. Cl. .................. 514/317; 514/345; 546/192; 546/255; 546/217; 546/261
[58] Field of Search ............... 546/217, 261, 255, 192; 514/317, 345

[56] References Cited

U.S. PATENT DOCUMENTS

| | | | |
|---|---|---|---|
| 4,414,219 | 11/1983 | Martin | 546/216 |
| 4,663,328 | 5/1987 | Lafon | 514/277 |

FOREIGN PATENT DOCUMENTS

| | | |
|---|---|---|
| 0156433 | 10/1985 | European Pat. Off. . |
| 0192521 | 8/1986 | European Pat. Off. . |
| 0192522 | 8/1986 | European Pat. Off. . |
| 0304330 | 2/1989 | European Pat. Off. . |
| 0372776 | 6/1990 | European Pat. Off. . |
| 2416886 | 9/1979 | France . |
| 2518093 | 6/1983 | France . |
| 2576898 | 8/1986 | France . |
| 2904826 | 8/1979 | Germany . |

OTHER PUBLICATIONS

Also Balsamo et al., "An approach to the knowledge of the steric requirements for alpha-adrenoreceptor direct activation alpha-Adrenergic properties of new 3-piperidinols", European Journal of Medicinal Chemistry.Chimica Therapeutica, vol. 16, No. 2, 1981, pp. 163–169, 1981.

Zlata Raza et al., "Preparation and properties of some prochiral and chiral precursors of S-3-(3-hydroxyphenyl)-1-propylpiperidine (S-3-PPP )...", Croatica Chemica Acta, vol. 64, No. 1, pp. 65–77, 1991.

*Primary Examiner*—Ceila Chang
*Assistant Examiner*—D. Margaret M. Mach
*Attorney, Agent, or Firm*—Jacobson, Price, Holman & Stern

[57] ABSTRACT

The invention relates to a compound of formula:

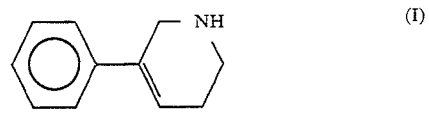

and its addition salts with pharmaceutically acceptable acids.

These compounds are useful in therapy as sedatives.
Figure none

3 Claims, No Drawings

1,2,5,6-TETRAHYDROPYRIDINE DERIVATIVE, PROCESS FOR PREPARING IT AND ITS APPLICATIONS IN THERAPY

The present invention relates to a new 1,2,5,6-tetrahydropyridine derivative, to a process for preparing it and to its applications in therapy, in particular as a sedative.

In EP-A-0,192,521, a description has already been given of compounds of formula:

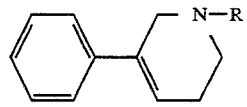

in which R is a $C_2$–$C_4$ alkyl group, and especially N-isopropyl-3-phenyl-1,2,5,6-tetrahydropyridine possessing activity with respect to the central nervous system, and to their use in therapy as sedative agents.

In FR-2,416,886, derivatives of the 3-[3-(trifluoromethyl)phenyl]-1,2,5,6-tetrahydropyridine type have, moreover, been described as having anorexigenic properties.

The present invention relates to the provision of a new 1,2,5,6-tetrahydropyridine derivative possessing sedative properties with a markedly improved affinity for $\alpha_2$ receptors.

The subject of the present invention is, more especially, a compound of formula:

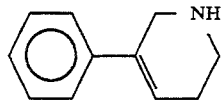

that is to say 3-phenyl-1,2,5,6-tetrahydropyridine, and its addition salts with pharmaceutically acceptable acids.

"Addition salts with pharmaceutically acceptable acids" denote salts which give the biological properties of the free bases without having an adverse effect. These salts can be, in particular, those formed with inorganic acids such as hydrochloric acid, hydrobromic acid, sulphuric acid, nitric acid and phosphoric acid, acidic metal salts such as disodium orthophosphate and mono-potassium sulphate and organic acids such as formic acid, acetic acid, propionic acid, glycolic acid, oxalic acid, fumaric acid, maleic acid, citric acid, malonic acid, methanesulphonic acid, lactic acid, succinic acid and tartaric acid.

The compound according to the present invention may be prepared by dehydration of a compound of formula

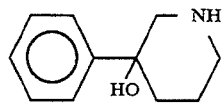

The dehydration may be carried out, in particular, using para-toluenesulphonic acid.

The compound of formula II has been described in EP-A-0,192,521.

The salts may be obtained in a conventional manner by reacting a compound of formula I with a pharmaceutically acceptable acid in a suitable solvent.

The example which follows illustrates the preparation of a compound according to the invention.

EXAMPLE 1:

Preparation of 3-phenyl-1,2,5,6-tetrahydropyridine hydrochloride (CRL 41711)

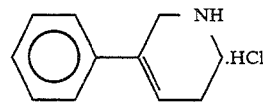

The $C_6H_6$—$H_2O$ azeotrope is distilled from a mixture of 8.3 g (0.047 mol) of 3-phenyl-3-hydroxypiperidine, 19.72 g (0,104 mol) of para-toluenesulphonic acid monohydrate and 200 ml of $C_6H_6$.

The mixture is alkalinized with 30 ml of $H_2O + 10$ ml of caustic soda, and the benzene is separated after settling has taken place, washed with water, dried over $MgSO_4$ and filtered. The benzene is evaporated off to dryness, the residue is taken up with ether, the mixture is acidified with ethanolic hydrogen chloride and the crystals are filtered off and recrystallized in acetone+ethanol.

5 g of product having a melting point of 214° C. are obtained (Yield = 54%).

Pharmacological and toxicological results demonstrating the advantageous properties of the compound of formula I are given below:

I—Pretoxicity:

Pretoxicity studies were performed in NMRI mice (3 animals per dose) with increasing doses of 16, 32, 64, 128, 256 and 512 mg/kg of products administered intraperitoneally. The dose causing the death of the three animals tested is given.

| Compound | mg/kg IP |
|---|---|
| Example 1 | 128 |

II—Sedative effect:

a) Action on spontaneous motility in mice

Half an hour after receiving the test compound intraperitoneally, the mice are placed in an activity-measuring device, where their motility is recorded over 30 minutes.

With the compound of Example 1, a significant decrease in locomotion is observed at and above a dose of 0.032 mg/kg.

b) Action on intergroup aggressive behaviour

After spending 3 weeks in each of the halves of a cage separated by an opaque partition, groups of 3 mice receive the test compound. Half an hour later, the two groups in the same cage are brought together by withdrawing the partition, and the number of fights occurring in the course of 10 minutes is noted.

At and above a dose of 0.032 mg/kg, but most particularly at a dose of 0.125 mg/kg, the compound of Example 1 decreases the number of fights.

c) Affinity for the $\alpha_2$ receptors of rat cerebral cortex

—Method:

Rats (male, $CD_1$, Sprague-Dawley, 200–250 g) are sacrificed by decapitation. The cerebral cortex is immediately removed. The cerebral cortices of 4 rats are homogenized in 40 ml of buffer. The homogenates are centrifuged at 20,000 rpm for 15 minutes. The pellet is resuspended in 40 ml of buffer and subjected to a second centrifugation (20,000 rpm for 15 minutes). The pellet thereby obtained is suspended in 8 ml of buffer and then stored at −80° C. until used. On the day of the experiment, a membrane suspension is prepared from the frozen suspension. Aliquots of this membrane suspension are mixed with radioactive ligands (used as marker for each type of receptor) and with increasing concentrations of the test compound, and then incubated (final volume: 1 ml). Reaction is stopped by filtration through a 48-hole HARVESTER system (WHATMAN GF/B filter strip). The filter strip is then washed 3 times with 5 ml of buffer and thereafter placed in an automatic cutting system (BRANDEL). The cut filters fall into counting vials and 4 ml of scintillation fluid (Aquasafe 300, ZINSSER) are distributed automatically by the same system (BRANDEL). Each sample is subjected to counting of the radioactivity using a liquid scintillation counter (KONTRON). Three experimental series are carried out with the test compound, each experiment being carried out in duplicate.

The specific binding is defined as the difference between the total binding and the non-specific binding (displaced by an excess of non-radioactive ligand). The values obtained in counts per minute (cpm) are then converted into disintegrations per minutes (dpm) in accordance with the efficiency of the counter.

$IC_{50}$ is defined as the concentration of the substance under study which is needed to displace 50% of the specifically bound radioactive marker.

The experimental data are analysed by means of LIGAND* software, which calculates the 50% inhibitory concentration ($IC_{50}$).

The results obtained using [$^3$H]clonidine as marker are given below.

| Test compound | $IC_{50}$ (mol/l) |
|---|---|
| Compound of Example 1 (CRL 41 711) | $2.6 \times 10^{-8}$ |
| Compound of Example 1 of EP-A-0,192,521 (CRL 41 244) | $70 \times 10^{-8}$ | d) Interaction with yohimbine in mice

Yohimbine administered intraperitoneally at a dose of 1 mg/kg decreases the hypomotility induced by the compound of Example 1 administered i.p. at doses of 0.5 and 2 mg/kg.

Similarly, yohimbine administered intraperitoneally at a dose of 0.5 mg/kg decreases the hypothermia induced by the compound of Example 1 intraperitoneally at doses of 0.125 and 0.5 mg/kg.

Since yohimbine is known to be an $\alpha_2$-noradrenergic receptor blocker, these results confirm the action of the compound of Example 1 on $\alpha_2$ receptors.

The subject of the present invention is also therapeutic compositions comprising as active principle the compound of formula I or one of its addition salts with pharmaceutically acceptable acids.

The therapeutic compounds according to the invention may be administered to man or animals orally or parenterally.

They may be in the form of solid, semi-solid or liquid preparations. As an example, tablets, hard gelatin capsules, suppositories and injectable solutions or suspensions may be mentioned, as well as retard forms and slow-release implanted forms.

In these compositions, the active principle is generally mixed with one or more customary pharmaceutically acceptable excipients which are well known to a person skilled in the art.

The quantity of active principle administered naturally depends on the patient who is treated, the administration route and the severity of the disorder.

The present invention relates also to a process for the treatment of anxiety which comprises administering to a human in need thereof an effective amount of a compound selected from the compounds of formula:

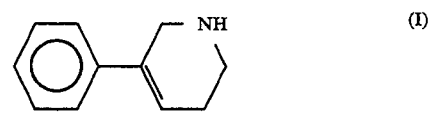

(I)

and its addition salts with pharmaceutically acceptable acids.

More specifically the compounds may be used for the treatment of generalized anxiety conditions and panic attack disorders (such as defined in DSM III-R) in humans. For such treatments the compounds may be used at a dosage of 1 to 100 mg/day.

I claim:

1. A compound selected from the compound of formula:

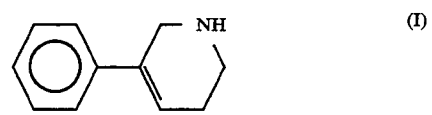

(I)

and its addition salts with pharmaceutically acceptable acids.

2. A therapeutic composition having a sedative activity comprising an effective amount of a compound selected from the compounds of formula:

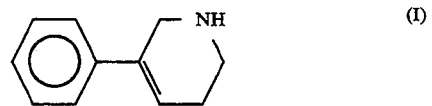

(I)

and its addition salts with pharmaceutically acceptable acids, in admixture with a pharmaceutically acceptable excipient.

3. A process for the treatment of anxiety which comprises administering to a human in need thereof an effective amount of a compound selected from the compounds of formula:

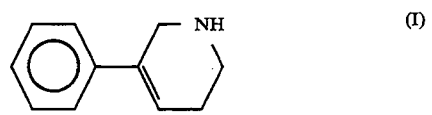

(I)

and its addition salts with pharmaceutically acceptable acids.

* * * * *